United States Patent
Otera

(10) Patent No.: US 9,459,209 B2
(45) Date of Patent: Oct. 4, 2016

(54) GAS ANALYSIS DEVICE

(75) Inventor: Fumiaki Otera, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 13/488,105

(22) Filed: Jun. 4, 2012

(65) Prior Publication Data

US 2013/0321815 A1 Dec. 5, 2013

(51) Int. Cl.
| | |
|---|---|
| *G01N 21/59* | (2006.01) |
| *G01N 21/61* | (2006.01) |
| *G01N 21/3504* | (2014.01) |
| *G01J 3/433* | (2006.01) |
| *G01N 21/39* | (2006.01) |
| *G01J 3/42* | (2006.01) |

(52) U.S. Cl.
CPC ............. *G01N 21/61* (2013.01); *G01J 3/42* (2013.01); *G01J 3/433* (2013.01); *G01N 21/3504* (2013.01); *G01N 21/39* (2013.01); *G01J 2003/4332* (2013.01); *G01N 2021/354* (2013.01)

(58) Field of Classification Search
CPC ............. G01N 21/3504; G01N 21/39; G01N 21/031; G01N 21/35; G01J 3/42; G01J 3/4338; G01J 2001/4242
USPC .......... 356/432–440, 244, 246; 250/343, 345, 250/339.11
See application file for complete search history.

(56) References Cited

U.S. PATENT DOCUMENTS

| | | | | |
|---|---|---|---|---|
| 5,173,749 | A * | 12/1992 | Tell et al. ...................... | 356/437 |
| 6,356,350 | B1 * | 3/2002 | Silver et al. .................. | 356/437 |
| 7,180,595 | B2 * | 2/2007 | Willing et al. ............... | 356/437 |
| 7,957,001 | B2 * | 6/2011 | Liu et al. ...................... | 356/435 |
| 8,094,313 | B2 * | 1/2012 | Kluczynski et al. ......... | 356/437 |

(Continued)

FOREIGN PATENT DOCUMENTS

| | | |
|---|---|---|
| JP | 05-099845 | 4/1993 |
| JP | 11-083665 | 3/1999 |

(Continued)

OTHER PUBLICATIONS

Japanese Office Action mailed Jun. 25, 2013 for corresponding Japanse Patent App. No. 2009-0276449.

(Continued)

*Primary Examiner* — Hoa Pham
(74) *Attorney, Agent, or Firm* — Morgan, Lewis & Bockius LLP

(57) ABSTRACT

If the specific gas concentration is relatively high, controller sets 0 as the modulation amplitude in a modulation amplitude controlling voltage generator for frequency modulation of laser light, controls a switching unit to select the output of a second ADC, and causes a computation unit to compute according to the direct absorption detection method to calculate the water molecule volume concentration. If the specific gas concentration is relatively low, the modulation amplitude is set to A, not 0, controls switching unit to select the output of a first ADC, which digitizes a synchronized detection signal, and causes the computation unit to compute according to the harmonic synchronous detection method to calculate the water molecule volume concentration. The concentration calculated using either of the methods is compared against a threshold value, and if decided that an accurate result cannot be obtained, the method is switched as the measurements are continuously executed.

2 Claims, 6 Drawing Sheets

(56) References Cited

U.S. PATENT DOCUMENTS

| | | | |
|---|---|---|---|
| 8,891,085 B2 * | 11/2014 | Otera | G01J 3/4338 356/326 |
| 9,007,592 B2 * | 4/2015 | Otera | G01J 3/42 356/437 |

FOREIGN PATENT DOCUMENTS

| | | | |
|---|---|---|---|
| JP | 2009192246 A | | 8/2009 |
| JP | 02010032454 A | * | 2/2010 |

OTHER PUBLICATIONS

English translation of "Reason for Rejection" for Japanese Office Action mailed Jun. 25, 2013 for corresponding Japanese Patent App. No. 2009-276449.

* cited by examiner

GAS ANALYSIS DEVICE

TECHNICAL FIELD

The present invention relates to a gas analysis device that uses the absorption of laser light to measure the concentration of a specific gas in a gas to be measured.

BACKGROUND ART

A method that has been proposed in recent years for measuring the concentration of a specific gas in a gas is laser adsorption spectroscopy, which uses absorption of wavelength-variable laser light (see for example Patent Literature 1). With this method, a sample cell where the gas to be measured is introduced is irradiated with laser light with a predetermined wavelength and the laser light that is transmitted is analyzed to determine the concentration of a specific gas in the gas based on the amount of absorption. Because, with this device, the light reception unit serving as a sensor does not contact the gas to be measured, the device offers a number of advantages including extremely short response time and the ability to perform measurements without disrupting the sample field.

Among infrared absorption spectroscopy that uses laser light such as the afore-described, spectroscopy that uses harmonic detection such as second harmonics is known as a detection method with a particularly high sensitivity (see for example Non-Patent Literature 1). The theory behind the detection method described in Non-Patent Literature 1 is briefly described next using, as an example, the detection of minute concentration of water vapor in nitrogen gas.

If the sample gas is at atmospheric pressure, the shape of the absorption property is represented by a Lorentz profile, and the relationship between water vapor concentration and the detected intensity of the received laser light is represented by equation (1) below.

Equation 1

$$\log\left(\frac{I_0(v)}{I(v)}\right) = c \times L \times S \times \frac{\gamma_L}{\pi([v-v_0]^2 + \gamma_L^2)} \quad (1)$$

Here, $I_0(v)$ represents the intensity of incident light at frequency $v$, and $I(v)$ represents the intensity of transmitted light at frequency $v$. $c$ represents the volume concentration of water molecules, $L$ the length of the optical path passing through the gas to be measured, and $S$ the predetermined linear strength of absorption property, and $\gamma_L$ the half-width of the absorption property, which is determined by the type of sample gas, temperature and pressure. $v_0$ represents the center frequency for the frequency modulation.

Equation (2) below represents the absorption intensity $I(v_0)$ at the center frequency.

Equation (2)

$$\log\left(\frac{I_0(v)}{I(v)}\right) = c \times L \times S \times \frac{1}{\pi\gamma_L} \quad (2)$$

Infrared absorption by water molecules in very low total pressure regions (high vacuum regions where the total pressure of the gas to be measured is less than 1 Torr) results in the width of the absorption property to be narrower than the width of the aforesaid Lorentz profile by a factor of several fold to several dozen fold. The width of the absorption property in said total pressure region is primarily determined by the Doppler effect. The shape of the absorption property is represented by a Gaussian line shape, and the relationship between the detected intensity of the received laser light and water vapor concentration is represented by equation (3) below.

Equation 3

$$\log\left(\frac{I_0(v)}{I(v)}\right) = c \times L \times S \times \frac{1}{\gamma_{ED}\sqrt{\pi}} \times \frac{1}{\exp\left(\frac{v-v_0}{\gamma_{ED}}\right)^2} \quad (3)$$

In equation (3), $\gamma_{ED}$ is referred to as the Doppler width and depends on the center frequency of the absorption frequency, molecular weight and temperature. Here, the absorption intensity $I(v_0)$ at center frequency $v_0$ is represented by equation (4) below.

Equation 4

$$\log\left(\frac{I_0(v)}{I(v)}\right) = c \times L \times S \times \frac{1}{\gamma_{ED}\sqrt{\pi}} \quad (4)$$

Under conditions of a high vacuum and room temperature of approximately 25° C., with an absorption spectrum in a region of relatively strong absorption that allows the use of an ordinary near-infrared semiconductor laser, $\gamma_{ED}$ is approximately equal to 0.01 cm$^{-1}$. With water molecules that are present in air or nitrogen matrix at 1 atmospheric pressure, the general value of $\gamma$ is 0.1 cm$^{-1}$.

Performing harmonic detection requires modulation of the frequency of light that is irradiated onto the gas to be measured. Letting "a" represent the modulation amplitude of the sine wave signal for frequency modulation and w represent frequency, the frequency of light at time t is defined by equation (5) below.

Equation 5

$$v \bmod(t) = v + a \cdot \cos \omega t \quad (5)$$

With second harmonic detection, signal components that correspond to twice the frequency or $2\omega$ are extracted. The second harmonic detection signal at center frequency $v_0$ for water molecules that are present in air or nitrogen at 1 atmospheric pressure is defined by equation (6) below.

Equation 6

$$\frac{\text{signal}(v_0)}{I_0} = c \times L \times S \times \frac{2}{\pi} \times \int_0^\pi \frac{\cos(2\theta)}{\left(\frac{a\cos\theta}{\gamma}\right)^2 + 1} d\theta \quad (6)$$

Similarly, the second harmonic detection signal at center frequency $v_0$ for water molecules in a vacuum atmosphere is defined by equation (7) below.

Equation 7

$$\frac{\text{signal}(v_0)}{I_0} = c \times L \times S \times \frac{2}{\gamma_{ED}\sqrt{\pi}} \times \int_0^\pi \frac{\cos(2\theta)}{\exp\left(\frac{a\cos\theta}{\gamma_{ED}}\right)^2} d\theta \quad (7)$$

These equations are proposed in Non-Patent Literature 2, which also proves that signal ($v_0$) with the highest sensitivity is obtained when the modulation amplitude a is selected so that a/γ (or a/$γ_{ED}$)=2.2 in equations (6) and (7).

The afore-described harmonic synchronous detection method has the advantage of high sensitivity but also has the problem of a narrow dynamic range of sensitivity. To explain, if the concentration of the gas to be measured is low, an accurate detection result can be obtained, but if the concentration of the gas to be measured becomes high, signal intensity becomes saturated, and accurate results cannot be obtained. For this reason, if the concentration of a specific gas in a gas to be measured has to be continuously measured and if the variation in concentration of the specific gas is large, there is a risk that the measurement range will be exceeded.

PRIOR ART LITERATURE

Patent Literature

Patent Literature 1: Unexamined Patent Application Publication No. Hei 5-99845
Patent Literature 2: Unexamined Patent Application Publication No. Hei 11-83665

Non-Patent Literature

Non-Patent Literature 1: C. R. Webster, "Infrared Laser Absorption: Theory and Applications in Laser Remote Chemical Analysis," Wiley, New York, 1988
Non-Patent Literature 2: G. V. H. Wilson, "Modulation Broadening of NMR and ESR Line Shapes," J. Appl. Phys., Vol. 34, No. 11, pp. 3276 (1963)

OVERVIEW OF THE INVENTION

Problems to Be Solved by the Invention

The present invention was made in light of the afore-described problems, and it is the object of the present invention to provide a gas analysis device that uses the laser absorption method to measure the concentration of a specific gas in the gas to be measured over a wide dynamic range.

Means for Solving the Problems

The present invention, which was made to solve the afore-described problems, is a gas analysis device comprising: a sample cell where gas to be measured is introduced; a laser irradiation unit and a light reception unit disposed outside of the sample cell; wherein laser light emitted from the laser irradiation unit is detected by the light reception unit after passing through the gas to be measured in the sample cell; and a concentration of a specific gas that is included in the gas to be measured is calculated based on a detection signal; and further comprising:
a) a modulation switching means that switches between a state where laser light that is emitted from the laser irradiation unit is modulated using frequency f and a state where the laser light is not modulated;
b) a first measurement means for synchronously detecting the detection signal from the light reception unit using a frequency that is an integer-multiple of the frequency and calculating the concentration of a specific gas based on the detection result if modulation is set by the modulation switching means;
c) a second measurement means for directly detecting the detection signal from the light reception unit without performing a synchronous detection and calculating the concentration of a specific gas based on the detection result if no modulation is set by the modulation switching means; and
d) a control means for controlling the modulation switching means and the first and second measurement means so that the concentration is measured by the first measurement means if the concentration of the specific gas is relatively low and the concentration is measured by the second measurement means if the concentration of the specific gas is relatively high.

With the gas analysis device according to the present invention, the concentration measurement that is performed by a first measurement means with modulation performed by the modulation switching means is based on the afore-described harmonic synchronous detection method. The concentration measurement that is performed by a second measurement means without modulation performed by the modulation switching means is based on direct absorption of light of a predetermined wavelength by a specific gas. While the harmonic synchronous detection method has a high sensitivity, if the concentration is high, it suffers from signal saturation. On the other hand, with the detection method that uses direct absorption, even though the sensitive is relatively low, signal saturation does not occur even if the concentration is high. With the gas analysis device according to the present invention, because the two afore-described detection methods are suitably selected depending on the concentration of a specific gas, the disadvantages of the two detection methods are compensated, thus enlarging the range of concentration over which measurements can be performed.

With one mode of a gas analysis device according to the present invention, the control means determines the concentration that is obtained from the first or second measurement means either with or without modulation, and a decision is made based on the determination result to either continue with or without the modulation, or to switch. The judgment criteria to be used for the concentration, i.e., the threshold value, can be experimentally set in advance depending on the type of specific gas.

This allows, when continuously measuring the concentration of a specific gas in a gas to be measured, to successively select the appropriate detection method in response to variations in concentration even if the concentration were to vary greatly, thus allowing the concentration value to be accurately and continuously monitored.

With the present invention, the type of specific gas that is measured does not matter, but since the present invention is effective where the concentration varies widely, it is effective for measuring, for example, moisture concentration in a gas to be measured.

Effects of the Invention

With the gas analysis device according to the present invention, the concentration of a specific gas in a gas to be measured can be measured in real time over a wide dynamic range of concentration. When continuously measuring, for example, the moisture concentration in a gas to be measured, this allows the user to be promptly notified of the accurate results of the concentration measurement even if the moisture concentration were to vary widely.

Also, ordinarily, calculating the concentration using the harmonic synchronous detection method required calibration in advance using a standard gas of a known concentration. However, with the gas analysis device according to the present invention, because the absorption spectrum is directly measured if the concentration of the specific gas were high, calibration can be performed by comparing the result of the absorption spectrum that is directly measured against a standard database (typically, HITRAN). This obviates the need for calibration using a standard gas and provides labor-saving in the measurement work, both of which are additional benefits provided by the present invention.

MODES FOR PRACTICING THE INVENTION

Figure 1:
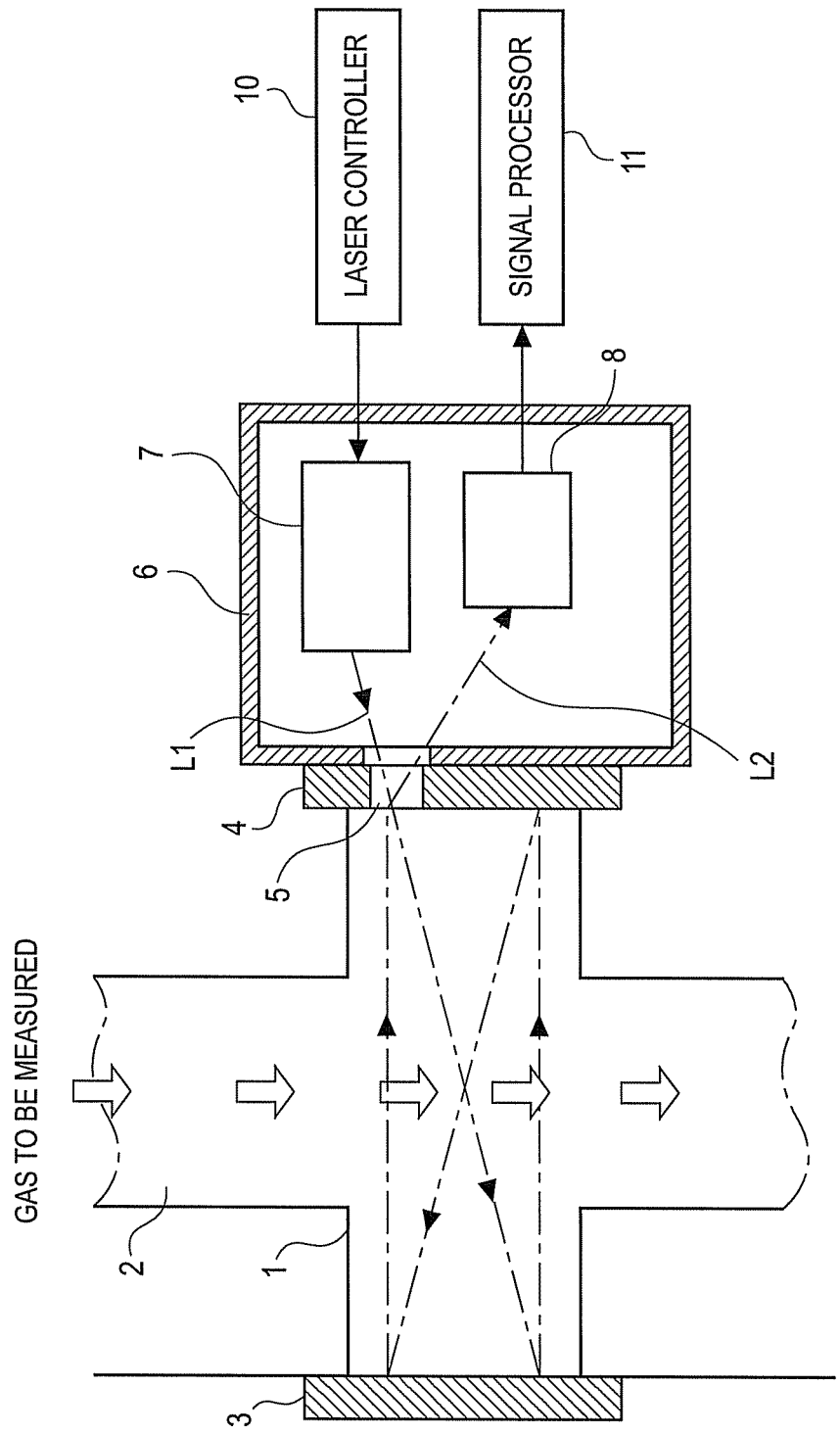
FIG. 1 shows a schematic view of the configuration of the measurement optical system in one embodiment of a moisture measurement instrument according to the present invention.
Figure 2:
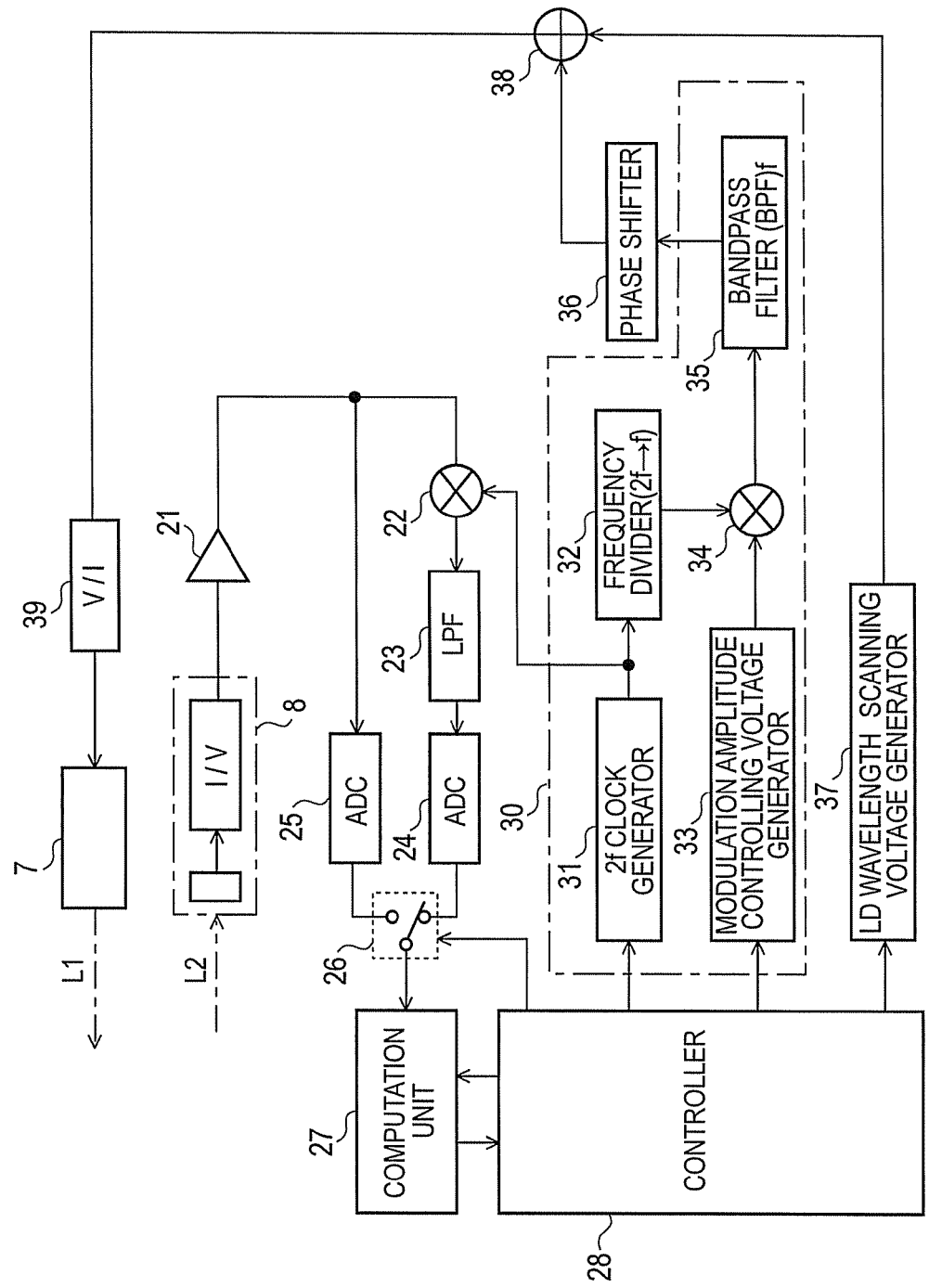
FIG. 2 shows a schematic view of the configuration of the signal processing system and control system in the present embodiment of a moisture measurement instrument.

One embodiment of a gas analysis device according to the present invention is described next with reference to the attached drawings. This embodiment is a moisture measurement instrument used for measuring moisture concentration in a gas to be measured. FIG. 1 shows a schematic view of the configuration of a measurement optical system in the present embodiment of a moisture measurement instrument. FIG. 2 shows a schematic view of the configuration of the signal processing system and control system in the moisture measurement instrument.

With the present embodiment of a moisture measurement instrument, a sample cell 1 that extends in a substantially horizontal direction is situated in a gas flow path 2 through which the gas to be measured flows in the top to bottom direction. Reflection mirrors 3 and 4 that oppose each other are disposed at the left and right open ends of sample cell 1. A transparent window 5 through which only light can pass is formed in one reflection mirror 3. Located on the outside of sample cell 1 with the transparent window 5 interposed in between is optical chamber 6 having a substantially sealed structure and its atmosphere at substantially atmospheric pressure. Disposed within said optical chamber 6 are wavelength-variable laser device 7 serving as a laser irradiation unit and photodetector 8 serving as a light reception unit. An example of a wavelength-variable laser device 7 is a DFB (distributed feedback) laser whose wavelength is in the near-infrared region to mid-infrared region, but other laser devices can be used as well. The photodetector 8 includes a photoelectric conversion device such as a diode and an I/V conversion amplifier that converts a current signal obtained by the photoelectric conversion device to a voltage signal. The moisture (interfering moisture) present within the optical chamber 6 is eliminated by a purge gas or a dehumidifying agent, and its concentration is reduced to a negligible level.

Laser light L1 that is emitted from wavelength-variable laser device 7 under the control of laser controller 10 passes through the transparent window 5 and enters the sample cell 1 and is repeatedly reflected by reflection mirrors 3 and 4. With the example of the optical path shown in FIG. 1, the laser light traverses across gas flow path 2 and makes two complete round-trips between reflection mirrors 3 and 4. However, the optical system can be constructed so that more complete round-trips are made. As the laser light travels through the gas flow path 2, the laser light is absorbed by various components that are included in the gas to be measured. The laser light L2 after the absorption by the various components passes through transparent window 5, returns to the optical chamber 6 and reaches the photodetector 8 where it is detected and output as an electrical signal that is input to signal processor 11. With the example shown in FIG. 1, the same transparent window 5 is used for both the emission from and incidence to sample cell 1 of the laser light. It is however also acceptable to provide separate transparent windows for the two purposes.

As shown in FIG. 2, the voltage signal that is obtained from photodetector 8 is amplified by amplifier 21 and is provided to synchronous detector 22 and a second analog/digital converter (ADC) 25. A clock signal with frequency 2f that is generated by a 2f clock generator 31, further described below, is input to the synchronous detector 22 as a reference signal. From the detection signal that is input to the synchronous detector 22 via the amplifier 21, the synchronous detector 22 extracts a signal that is in synchrony with the phase and frequency of the reference signal. Low-pass filter (LPF) 23 removes high-frequency components from the synchronized detection signal, which is then converted into a digital signal by a first analog/digital converter (ADC) 24. Switching unit 26 selects either the output of the first ADC 24 or the output of the second ADC 25, which has not been passed through the synchronous detector 22, and inputs the output to a computation unit 27.

The 2f clock generator 31, frequency divider 32, modulation amplitude controlling voltage generator 33, multiplier 34 and bandpass filter (BPF) 35 constitute a sine wave generator 30 of frequency f whose modulation amplitude can be optionally set. To explain, under the control of controller 28, the 2f clock generator 31 generates a clock signal with frequency 2f, and frequency divider 32 divides the frequency of the clock signal by two and generates a clock signal with frequency f and a duty ratio of 50%. The modulation amplitude controlling voltage generator 33 includes a digital/analog converter that converts the digital data provided by controller 28 to analog values and outputs a DC voltage that corresponds to the modulation amplitude. The DC voltage and the clock signal with frequency f are multiplied by multiplier 34. The clock signal after the multiplication has a frequency f and an amplitude that is determined by the DC voltage. The BPF 35, which has a predetermined passband with center frequency f, converts a square-wave clock signal with center frequency f to a sine wave signal with center frequency f. The sine wave signal is used as the modulation signal for the frequency modulation. Instead of using a configuration such as this, it is also acceptable to use a conversion performed by a digital/analog converter to directly generate a sine wave with frequency f.

The LD wavelength scanning voltage generator 37, which includes a digital/analog converter, converts the digital data that is output by controller 28 for sweeping across a predetermined wavelength region close to the absorption spectrum of water molecules to a sweep voltage and outputs the sweep voltage. The phase of the sine wave signal from the aforesaid BPF 35 is shifted by phase shifter 36 to be in synchrony with the detection signal. The sine wave signal is then added to the aforesaid sweep voltage by adder 38. The voltage with the sine wave signal superimposed on the sweep voltage is converted to a current signal by voltage/current converter (V/I) 39 and is supplied to wavelength-variable laser device 7 as a drive current. The wavelength-variable laser device 7 emits laser light L1 that is frequency modulated using a predetermined modulation amplitude and whose wavelength changes with passage of time.

With the present embodiment of a moisture measurement instrument, controller 28 outputs digital data to modulation amplitude controlling voltage generator 33 that causes the amplitude of the sine wave signal generated by the sine wave generator 30 to switch between 0 and a predetermined value (value "A") which is not 0. The switching unit 26 is controlled so that the output of first ADC 24 is selected to make the amplitude of the sine wave signal equal to A and to select the output of the second ADC 25 to make the amplitude of the sine wave signal equal to 0. The processing algorithm used by computation unit 27 is also switched. To explain, when the amplitude of the sine wave signal is set to A, the concentration is calculated based on the harmonic synchronous detection method, and when the amplitude of the sine wave signal is set to 0, the concentration is calculated based on spectrum detection by direct absorption ("direct absorption detection method").

Figure 5A:
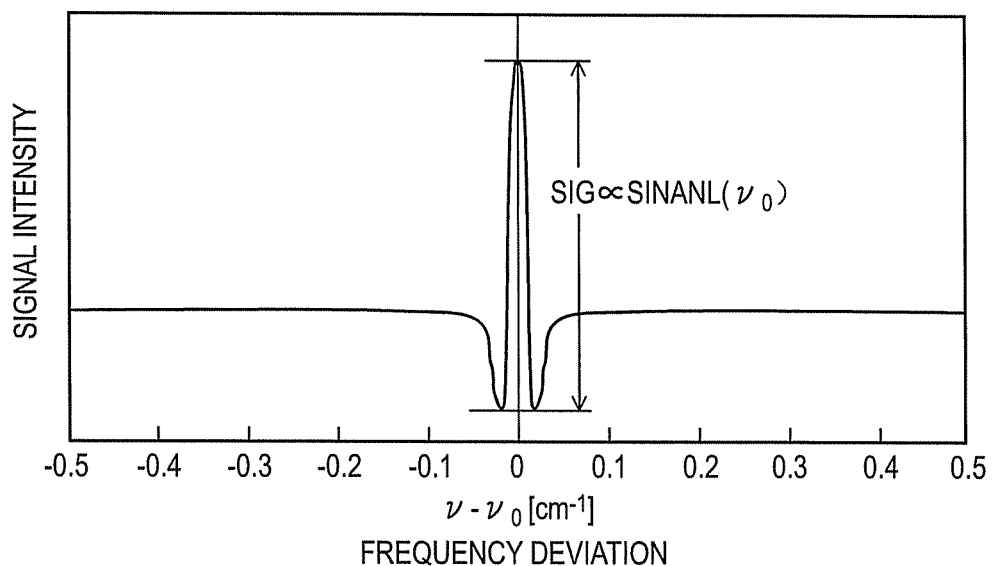
FIG. 5 shows examples of signal waveforms that are obtained with the harmonic synchronous detection method and the direct absorption detection method.
Figure 5B:
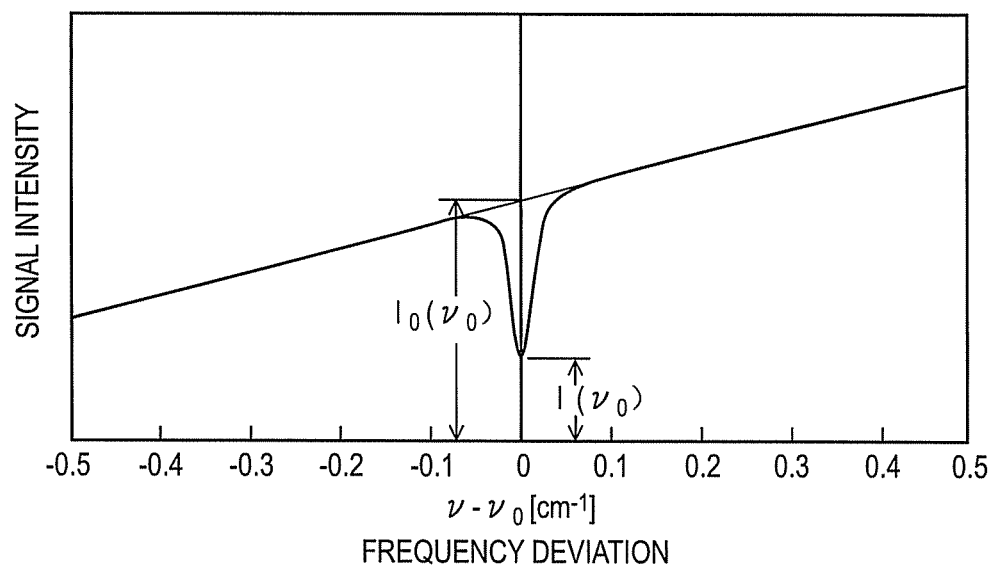

FIGS. 5(*a*) and (*b*) show examples of signal waveforms that are obtained by calculation (simulation) based on the harmonic synchronous detection method and direct absorption detection method. Frequency deviation $v-v_0$ is plotted along the horizontal axis and signal intensity is plotted along the vertical axis.

With the 2f synchronized detection signal shown in FIG. 5(*a*), the signal intensity at frequency deviation of zero, i.e., at center frequency $v_0$, shows the absorption intensity by the water molecules. However, with the synchronized detection signal that is obtained with the actual device, because the positive direction peaks and negative direction peaks that are shown in FIG. 5(*a*) are added, it is difficult to separate them computationally. For this reason, the peak-to-peak signal intensity SIG of the signal waveform becomes proportional to the value of signal ($v_o$) on the left side of equations (6) and (7). By determining in advance the proportionality constant B that defines the proportional relationship, the volume concentration c of the water molecules can be calculated from the signal intensity of the synchronized detection signal that is obtained.

With the signal that is based on the direct absorption detection method shown in FIG. 5(*b*), a peak is observed at a frequency deviation of zero, i.e., at center frequency $v_0$, where the signal intensity decreases due to absorption by water molecules. The volume concentration c of the water molecules can be calculated by applying to the aforementioned equation (2) or equation (4) the signal intensity $I_0(v_0)$ assuming no absorption and the signal intensity $I(v_0)$ at the absorption peak.

As for the aforesaid proportionality constant B, if the signal (output signal of 2f clock generator 31) with frequency f that is used for synchronous detection is a perfect sine wave, the proportionality constant B theoretically becomes 1. Even if the 2f signal is not a sine wave but is a square wave, the proportionality constant B can be determined in the following way. First, a specific gas with a relatively high moisture concentration is selected for measurement so that both the harmonic synchronous detection method and the direct absorption detection method can be used. Next, the volume concentration c of water molecules is calculated using the direct absorption detection method. The signal intensity based on the harmonic synchronous detection method is next determined. The proportionality constant B is then selected so that the volume concentration of water molecules based on the signal intensity matches the volume concentration of the water molecules determined by the direct absorption detection method. Needles to say, if the volume concentration of the water molecules can be determined by a method other than the direct absorption detection method or a gas with a known volume concentration of water molecules is available, the proportionality constant B can be determined so that the volume concentration of water molecules determined by the harmonic synchronous detection method matches the known volume concentration.

In general, the harmonic synchronous detection method is a more sensitive detection method than the direct absorption detection method and is extremely effective for detection of minute quantities. However, the harmonic synchronous detection method is not necessarily suitable for measurements where the gas concentration to be measured varies widely. For example, in addition to the measurement of moisture that is discussed here, to measure in a vacuum a gas such as oxygen, which is present in atmosphere, the range of measured concentration can vary by a factor of more than 1000. This exceeds the range of concentration that can be measured by the harmonic synchronous detection method. With the present embodiment of the moisture measurement instrument, measurements are performed in a sequence such as that shown in FIG. 3 so that volume concentration of moisture that varies over a wide measurement concentration range can be accurately, quickly and continuously measured.

When measurement is started, controller 28 starts the measurement with the modulation amplitude set to 0 (step S1). This sets the amplitude of the sine wave signal generated by the sine wave generator 30 to 0. A sweep voltage that spans a predetermined wavelength region close to the absorption spectrum of water molecules is applied to the voltage/current converter, and a corresponding drive current is supplied to the wavelength-variable laser device 7. The controller 28 also switches the switching unit 26 so that the output of the second ADC 25 is selected. The computation unit 27 receives data that is obtained by digitizing the detection signal (signal with a waveform such as that shown in FIG. 5(*b*)) that corresponds to the wavelength scanning and uses a processing algorithm for the direct absorption detection method to calculate volume concentration Ca of the water molecules (step S2). The controller 28 receives this result and determines whether the volume concentration Ca is equal to or less than a threshold value α set in advance (step S3). If the volume concentration Ca is greater than the threshold value α, a decision is made that the direct absorption detection method is suitable. The volume concentration Ca is adopted as the result (step S4) and the process returns to step S2.

In contrast to this, if the volume concentration Ca is equal to or less than the threshold value a, a decision is made that the direct absorption detection method is not sensitive enough. The volume concentration Ca is not adopted as the result, and the controller 28 sends data to modulation amplitude controlling voltage generator 33, which sets the modulation amplitude to A cm$^{-1}$ (step S5). The controller 28 also switches switching unit 26 so that the output of first ADC 24 is selected. In other words, a switch is made from the direct absorption detection method to the harmonic synchronous detection method. This causes the sine wave generator 30 to output a sine wave signal with frequency f and modulation amplitude of A. A voltage wherein the modulation signal is superimposed on the sweep voltage spanning across a predetermined wavelength region close to the absorption spectrum of the water molecules is applied to the voltage/current converter 39, and a corresponding drive current is supplied to the wavelength-variable laser device 7. The computation unit 27 receives data that is obtained by the digitization of a hat monic synchronized detection signal (signal with a waveform such as that shown in FIG. 5(a)) that corresponds to the wavelength scanning and uses the processing algorithm for the harmonic synchronous detection method to calculate the volume concentration Cb of the water molecules (step S6).

The controller 28, which receives this result, determines whether or not the volume concentration Cb is equal to or greater than threshold value $\beta$ that is set in advance (step S7). If the volume concentration Cb is less than the threshold value $\beta$, a decision is made that the harmonic synchronous detection method is suitable. The volume concentration Cb is adopted as the result (step S8), and the process returns to step S6. In contrast to this, if the volume concentration Cb is equal to or greater than the threshold value $\beta$, a decision is made that the concentration is too high and signal saturation will result with the harmonic synchronous detection method. The volume concentration Cb is not adopted as the result, the process returns to step S1, and the detection method is switched from the harmonic synchronous detection method to the direct absorption detection method.

The threshold value $\alpha$ and threshold value $\beta$ are suitably set in advance based on factors such as the signal to noise ratio of detection signals from the harmonic synchronous detection method and the direct absorption detection method and the signal saturation level with the harmonic synchronous detection method. By so doing, even if the volume concentration of water molecules in a gas to be measured were to vary widely during continuous measurement of the volume concentration of the water molecules, the detection method is promptly and correctly switched between the harmonic synchronous detection method and the direct absorption detection method, thus allowing an accurate concentration to be obtained.

Figure 3:
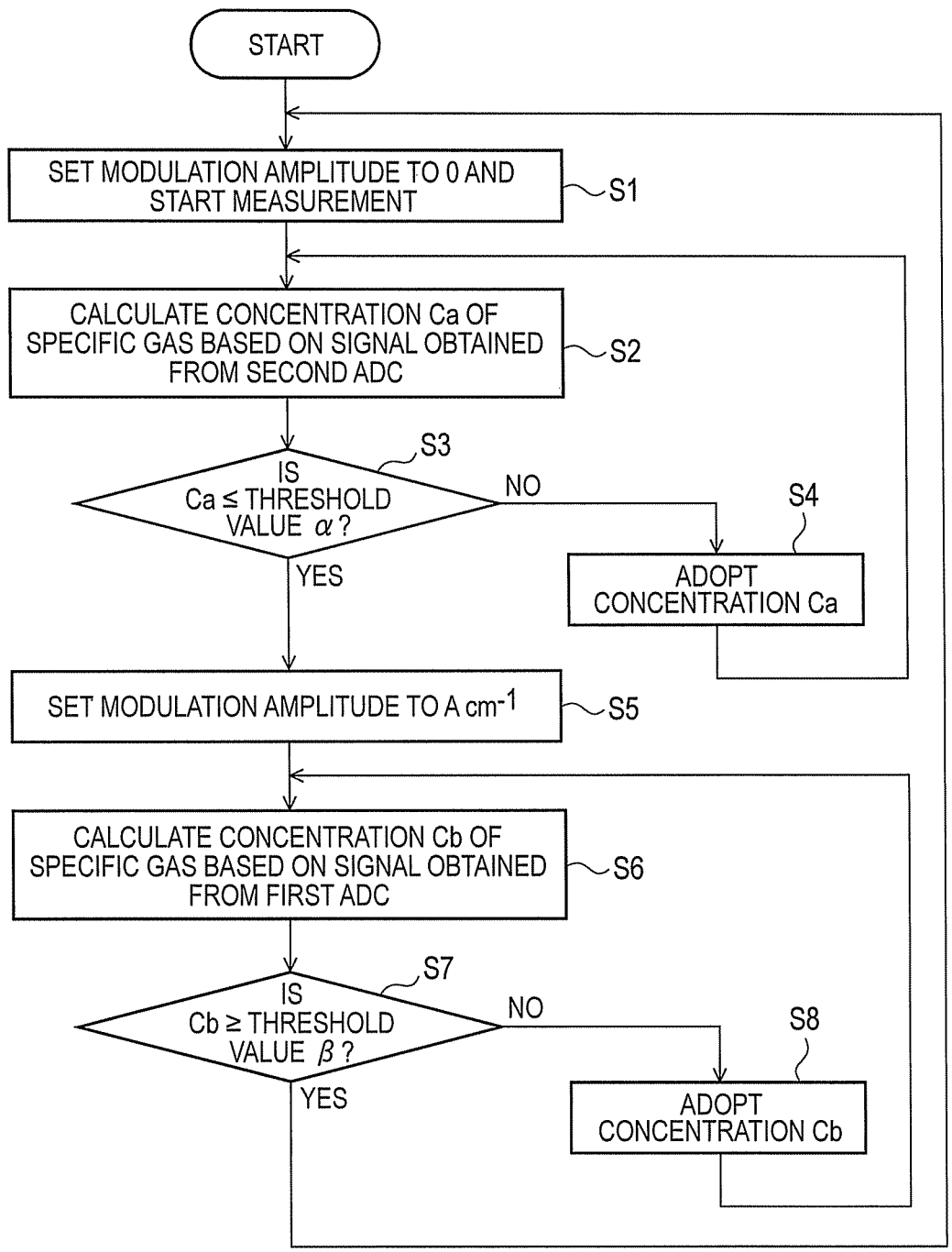
FIG. 3 shows a flowchart of the measurement sequence in the present embodiment of a moisture measurement instrument.
Figure 4:
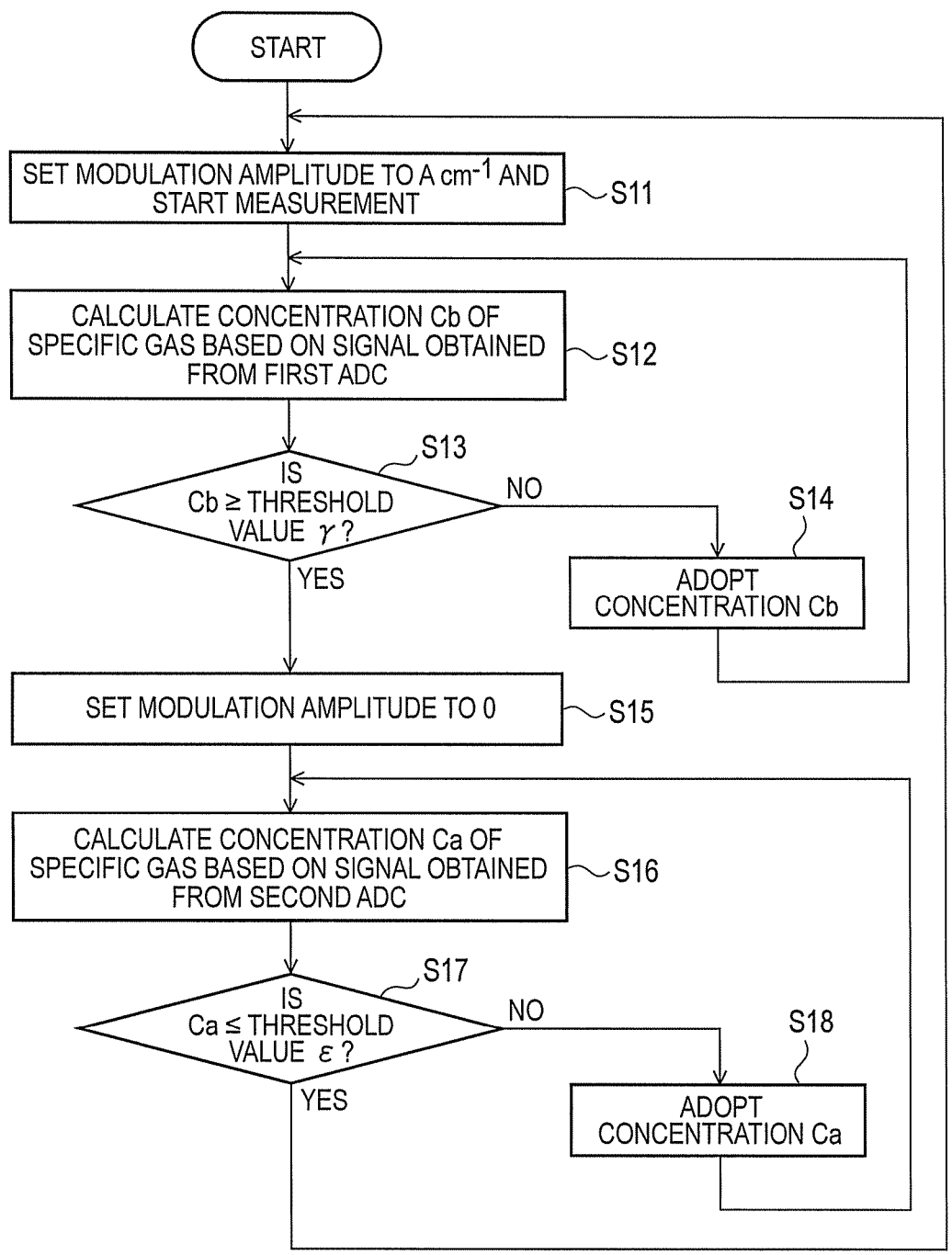
FIG. 4 shows a flowchart of another measurement sequence in the present embodiment of a moisture measurement instrument.

The sequence shown in FIG. 3 may be modified to the sequence shown in FIG. 4. To explain, unlike the sequence shown in FIG. 3, with the sequence shown in FIG. 4, when measurement is started, concentration measurement using the harmonic synchronous detection method is first performed (steps S11 and S12). If the concentration Cb is less than a threshold value $\gamma$ set in advance ("No" in step S13), the concentration Cb is adopted (step S14), and the harmonic synchronous detection method is continued to be used. On the other hand, if the concentration Cb is equal to or greater than the threshold value $\gamma$ set in advance ("Yes" in step S13), the detection method is switched to the direct absorption detection method, and the concentration is measured (steps S15 and S16). If the concentration Ca that is determined is equal to or less than a threshold value $\epsilon$ set in advance ("Yes" in step S17), the process returns to step S11. If the concentration Ca is greater than the threshold $\epsilon$, the concentration Ca is adopted (step S18), and the direct absorption detection method is continued to be used.

Figure 6:
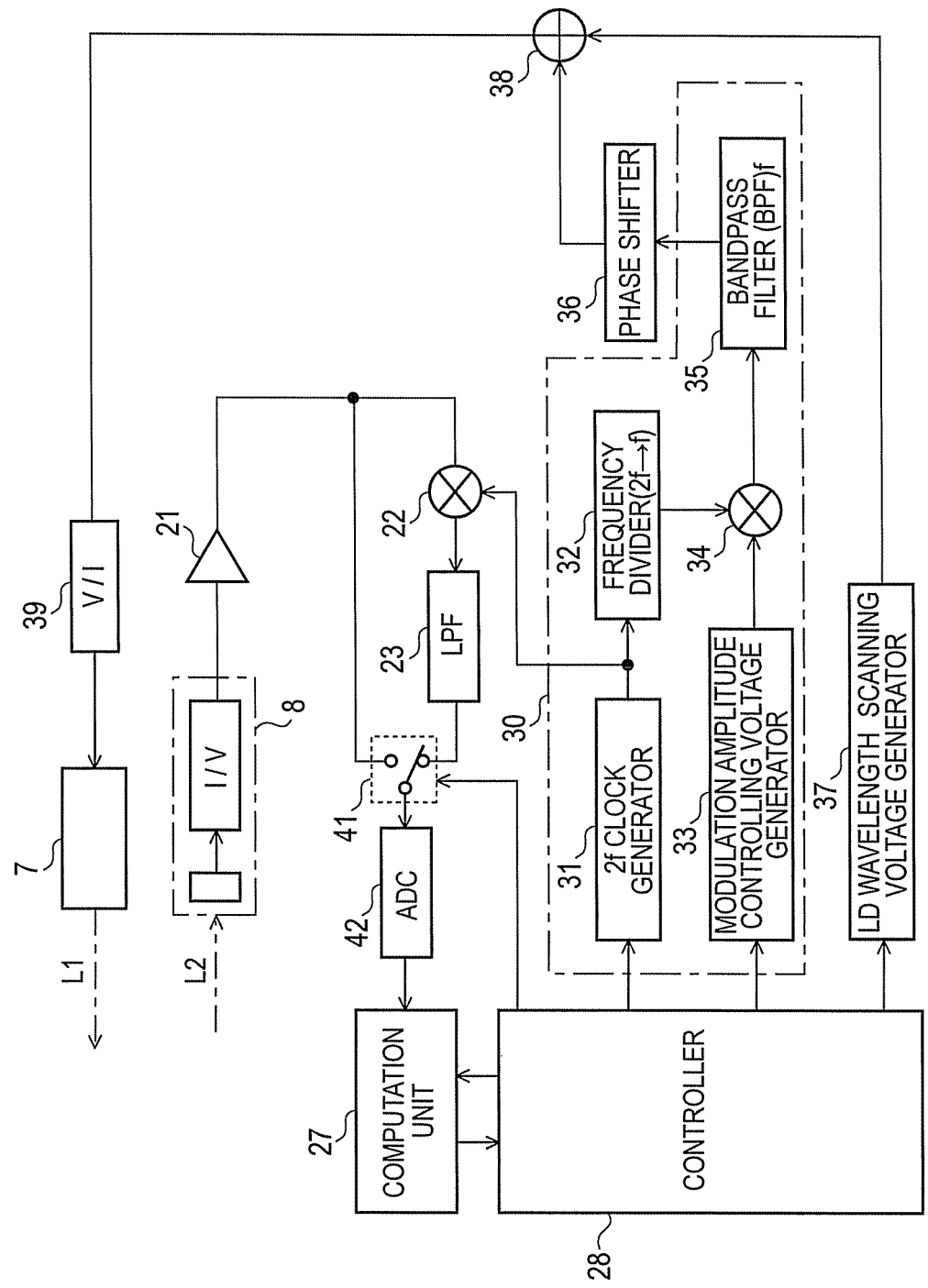
FIG. 6 shows a schematic view of the configuration of another embodiment of the signal processing system and control system according to the present invention.

With the afore-described embodiment of the moisture measurement instrument, a first ADC 24, which digitizes a synchronized detection signal, and a second ADC 25 that digitizes the original signal without synchronous detection are both provided. It is also possible to use a configuration where the ADC is shared. To explain, as shown in the block configuration diagram of FIG. 6, a switching unit 41 is provided in a stage before ADC 42. A switching unit 41 either selects a synchronized detection signal that has passed through synchronous detector 22 and LPF 23 or a detection signal without synchronous detection, and the selected signal is provided to a common ADC 42 for digitization. Even with this configuration, the basic operation is the same as that of the afore-described embodiment.

With the afore-described embodiments, the gas analysis device according to the present invention was used for the measurement of moisture concentration in a gas to be measured. However, the present invention can also be used to measure any gas concentration other than moisture. Needless to say, the values of afore-described modulation amplitude A, threshold values $\alpha$, $\beta$, $\gamma$ and $\epsilon$ and the like must be suitably changed depending on the type of specific gas.

The afore-described embodiments are just examples of the present invention, and modifications, additions, changes and the like can be made to matters not described above within the gist of the present invention and still be included within the claims of the present invention.

DESCRIPTION OF THE NUMERICAL REFERENCES

1. Sample cell
2. Gas flow path
3, 4. Reflection mirror
5. Transparent window
6. Optical chamber
7. Wavelength-variable laser device
8. Photodetector
10. Laser controller
11. Signal processor
21. Amplifier
22. Synchronous detector
23. Low-pass filter (LPF)
24, 25, 42. Analog/digital converter (ADC)
26, 41. Switching unit
27. Computation unit
28. Controller
30. Sine wave generator
31. 2f clock generator
32. Frequency divider
33. Modulation amplitude controlling voltage generator
34. Multiplier
35. Bandpass filter (BPF)
36. Phase shifter
37. LD wavelength scanning voltage generator
38. Adder
39. Voltage/current converter (V/I)

What is claimed is:
1. A gas analysis device, comprising:
a sample cell where gas to be measured is introduced;
a laser irradiation unit and a light reception unit disposed outside of said sample cell;
wherein laser light emitted from said laser irradiation unit is detected by said light reception unit after passing through the gas to be measured in said sample cell; and
a concentration of a specific gas that is included in the gas to be measured is calculated based on a detection signal;
a modulation switching means for switching between a state where laser light that is emitted from said laser irradiation unit is modulated using frequency f and a state where the laser light is not modulated;

a first measurement means for synchronously detecting the detection signal from said light reception unit using a frequency that is an integer-multiple of the frequency and calculating the concentration of a specific gas based on the detection result if modulation is set by said modulation switching means;

a second measurement means for directly detecting the detection signal from said light reception unit without performing a synchronous detection and calculating the concentration of a specific gas based on the detection result if no modulation is set by said modulation switching means; and a control means for controlling said modulation switching means and the first and second measurement means so that the concentration is measured by the first measurement means if the concentration of said specific gas is relatively low and the concentration is measured by the second measurement means if the concentration of said specific gas is relatively high, wherein said control means determines the concentration that is obtained from the first or second measurement means either with or without modulation and a decision is made based on the determination result to either continue with or without the modulation, or to switch.

2. The gas analysis device according to claim 1 wherein the specific gas is moisture in the gas to be measured.

* * * * *